United States Patent [19]

Roman

[11] 4,024,254
[45] May 17, 1977

[54] S-ESTERS OF NITRO(TETRAHYDRO-2H-1,3-THIAZIN-2-YLIDENE)ETHANETHIOIC ACID

[75] Inventor: Steven A. Roman, Oakdale, Calif.
[73] Assignee: Shell Oil Company, Houston, Tex.
[22] Filed: Mar. 11, 1976
[21] Appl. No.: 665,983
[52] U.S. Cl. .............................. 424/246; 260/243 R
[51] Int. Cl.$^2$ ...................................... C07D 279/06
[58] Field of Search ................. 260/243 R; 424/246

[56] References Cited

UNITED STATES PATENTS

| | | | |
|---|---|---|---|
| 3,962,225 | 6/1976 | Powell | 260/243 R |
| 3,962,233 | 6/1976 | Roman | 260/243 R |
| 3,962,234 | 6/1976 | Roman | 260/243 R |

FOREIGN PATENTS OR APPLICATIONS 43-11097  4/1973  Japan

OTHER PUBLICATIONS

Hirai et al., *Chem. Phar. Bull.*, vol. 20, pp. 97–101 (1972).

*Primary Examiner*—John M. Ford

[57] ABSTRACT

Novel insecticidal S-esters of nitro(tetrahydro-2H-1,3-thiazin-2-ylidene)ethanethioic acid.

3 Claims, No Drawings

S-ESTERS OF NITRO(TETRAHYDRO-2H-1,3-THIAZIN-2-YLIDENE)ETHANETHIOIC ACID

DESCRIPTION OF THE INVENTION

It has been found that useful insecticidal activity is possessed by certain S-esters of nitro(tetrahydro-2H-1,3-thiazin-2-ylidene)ethanethioic acid. These esters are resonance hybrids, the principal forms contributing thereto being described by the formulae

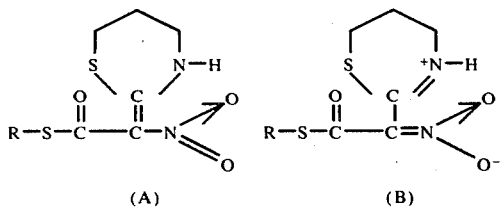

wherein the symbols have the respective meanings set out hereinafter.

These compounds also can exist in the corresponding tautomeric enol form which can be described by the formula

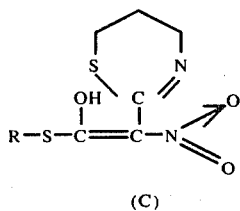

The resonance hybrids may exist as either of two geometric (cis-trans) isomers, depending upon the spatial relationship of the moieties about the bond between the carbon atom of the nitromethylene moiety and the ring carbon atom to which it is joined.

The enol form (Form C) can be designated as a 1-R-S-2-nitro-2-(5,6-dihydro-4H-1,3-thiazin-2-yl)vinyl alcohol. The left-hand form of the resonance hybrid (Form A) can be designated as an S-ester of nitro(tetrahydro-2H-1,3-thiazin-2-ylidene)ethanethioic acid. The right-hand form (Form B) can be designated as an 2-(R-thiocarbonyl-aci-nitromethyl)-5,6-dihydro-4H-1,3-thiazinium hydroxide inner salt.

In this specification, for the sake of simplicity, these compounds will be referred to generally as S-esters of nitro(tetrahydro-2H-1,3-thiazin-2-ylidene)ethanethioic acid. This terminology is intended to include all of the contributors to the resonance hydrid, the geometric isomers and the enol form, as well as mixtures thereof.

In these compounds, R contains up to thirty carbon atoms and is alkyl, alkenyl, alkynyl, cycloalkyl, cycloalkylalkyl, alkadienyl, haloalkyl, haloalkenyl, mono- and poly-(alkoxy)alkyl, alkylthioalkyl, phenylthioalkyl, benzylthioalkyl, cyanoalkyl, hydroxyalkyl, alkylsulfinylalkyl, alkylsulfonylalkyl, phenyl, phenalkyl, phenylalkenyl or any of these substituted on the ring by one to two of one or more of halogen, nitro, cyano, alkyl, phenyl, alkoxy, methylenedioxy or phenoxy; is aminoalkyl, -(CH$_2$)$_m$NR$^3$R$^4$, wherein $m$ is one or two, R$^3$ is alkyl, cycloalkyl, alkenyl, phenyl or phenalkyl, and R$^4$ is hydrogen or one of the moieties represented by R$^3$; or is -(CH$_2$)$_n$R$^5$, wherein $n$ is zero, one or two, and R$^5$ is a heterocyclic moiety selected from furanyl, tetrahydrofuranyl, dioxolanyl, thienyl, thiopyranyl, pyridinyl, pyrrolidinyl, morpholinyl, and their R$^5$-methyl- counterparts.

When aliphatic, the moiety represented by R may be of straight-chain or branched-chain configuration, and preferably contains no more than ten carbon atoms. The preferred aminoalkyl moieties are dialkylaminomethyl and -ethyl. The preferred aralkyl moieties are optionally-substituted phenylmethyl.

Also, the invention includes salts of the compounds described above, both salts and inner salts of the formula:

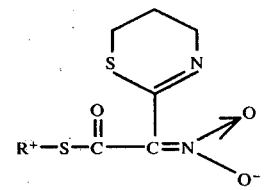

such as ammonium, sulfonium and pyridinium salts.

The contemplated salts include alkali metal salts, ammonium salts, pyridinium salts and amine salts generally, and particularly salts of alkyl- and alkanolamines, and polyamines. Included are the salts of mono-, di- and trialkyl, alkanol, alkenyl and mono- and poly-(alkoxy)alkylamines, and polyamines in which each alkyl, alkenyl, alkanol, or alkoxyalkyl moiety contains from one to twenty carbon atoms or more including, but not necessarily limited to, one or more of dimethylamine, diethanolamine, trimethylamine, oleyl propylenediamine, n-dodecylamine, n-tetradecylamine, n-hexadecylamine, n-octadecylamine, heptylamine, triethanolamine, tert-C$_{11-14}$ and tert-C$_{18-24}$ primary amines, oleylamine, coco amine, hydrogenated tallow amine, tallow amine, soya amine, dicoco amine and di(hydrogenated tallow) amines, dimethyl hexadecylamine, dimethyl octadecylamine, dimethyl coco amine, dimethyl soya amine, N-coco propylenediamine, N-soya propylenediamine, N-tallow propylenediamine, and the like.

For illustration, preparation of two typical particular species of the esters of the genus is described in the examples included hereinafter. Other typical particular species of this genus of esters include those wherein the symbol, R (referring to formulae A, B and C) represent the following moieties, this manner of naming these species being accurate, yet pointing out the differences between the different species more clearly than if the entire, complicated name of each species were to be given:

R = 3-cyanopropyl
cyclobutyl
cholesteryl
farnesyl
(1-methyl-2-piperidinyl)methyl
(1-methyl-2-pyrrolyl)methyl
(1-methyl-2-imidazolyl)methyl
2-thiazolylmethyl
2-oxazolylmethyl
2-pyrimidinylmethyl
2-(1-pyrrolidinyl)ethyl
benzylideneaminomethyl
heptyl 4-chlorobenzyl
isopropyl
isobutyl
n-butyl
allyl
2-propynyl
pentyl
2,2-dimethylpropyl
octyl
2-butenyl
2,2,2-trifluoroethyl
2-methoxyethyl
cyclopentyl
2-furanylmethyl
2-butynyl
4-methoxybenzyl
3-butynyl
3,7-dimethyl-2,6-octadienyl
1-methyl-2-propynyl
1-methyl-2-propenyl
hexyl
1-naphthalenylmethyl
tetrahydro-2-furanylmethyl
2-ethoxyethyl
2,2-dimethyl-1,3-dioxolan-4-ylmethyl
2-(2-methoxyethoxy)ethyl
3-phenoxybenzyl
3-butenyl
4-cyanobenzyl
cyclopropylmethyl
2,4-dichlorobenzyl
1-cyclopropylethyl
2-(1-naphthylenyl)ethyl
2-naphthylenylmethyl
(trans)-3-chloro-2-propenyl
(cis)-3-chloro-2-propenyl
2-methylthioethyl
2-thienylmethyl
isobornyl
2-(dimethylamino)ethyl; $CH_3I$ salt
cyclohexylmethyl
tetrahydro-2H-thiopyran-3-yl
menthyl
3-chloropropyl
2-hydroxyethyl
2-pyridinylmethyl; $CH_3I$ salt
norbornyl
3-chloro-2-propenyl
2-butoxyethyl
2-(4-morpholinyl)ethyl
2-(2-oxo-1-pyrrolidinyl)ethyl
2-(butylthio)ethyl
2-(ethylthio)ethyl
2-(phenylthio)ethyl
3-(methylthio)propyl
3-pyridinylmethyl; $CH_3I$ salt and inner salt thereof
2-methylsulfinylethyl
benzyl
4-chlorobenzyl
3,4-(methylenedioxy)phenyl
3-phenyl-2-propenyl
5-phenyl-2,4-pentadienyl
2-(benzylthio)ethyl
3-iodopropyl
phenyl
2-(dimethylamino)ethyl
2-quinolinylethyl
2-(methylsulfonyl)ethyl
2-(diphenylamino)ethyl
1-methyl-3-piperidinyl
1-benzyl-3-piperidinyl
(2,2,3,3-tetramethylcyclopropyl)methyl Compounds of this invention can be prepared by treating tetrahydro-(2-nitromethylene)-2H-1,3-thiazine with a 1-(R-thiocarbonyl)-3-methylimidazolium chloride by a method analogous to that described by E. Guibe-Jampel, et al., Bull. Soc. Chim. Fr. 1973 (3) (Pt. 2), pp. 1021-7. According to this method, the imidazolium chloride is prepared by treating 1-methylimidazole with the appropriate chlorothiolformate, R—S—C(O)—Cl, preferably in a suitable solvent and at a low temperature, for example, about 5° C. A suitable general method for conducting this procedure comprises adding a solution of the chlorothiolformate in tetrahydrofuran slowly (e.g., dropwise) to a cold (e.g., 5°) solution of the 1-methylimidazole in the same solvent, stirring the cold mixture for a period of from about 15 minutes to one hour to ensure complete reaction, then adding the thiazine to that stirred cold mixture/suspension, then warming the stirring mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatography).

The chlorothioformate reactants are in many cases known compounds, and in those cases when they are specifically novel, can be prepared by the procedures known in the art for the known analogs thereof.

This procedure for preparing compounds of this invention is illustrated in the following examples of the preparation of particular species of such compounds. In all cases, the identity of the product and of any intermediate employed was confirmed by appropriate analyses.

EXAMPLE 1 nitro(tetrahydro-2H-1,3-thiazin-2-ylidene)-ethanethioic acid, S-ethyl ester (1; R = ethyl)

Tetrahydro-2-(nitromethylene)-2H-1,3-thiazine (1B)

To a mixture of 235 g of 5,6-dihydro-2-(methylthio)-4H-1,3-thiazine (A. F. McKay et al., J. Am. Chem. Soc., 80, 3339 (1950)) and 2 g of zinc chloride at approximately 115° in a nitrogen atmosphere, 263 g of ethyl nitroacetate (S. Zen et al., Kogyo Kagaku Zosshi, 74, 70 (1971)) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled 2/1 ether/isopropyl alcohol mixture. The crystallized product was collected, washed with ether and dried under reduced pressure to leave a tan solid, m.p. 100°–102°, which on recrystallization from methanol gave ethyl nitro(tetrahydro-2H-1,3-thiazin-2-ylidene)acetate (1A), as a pale yellow solid, m.p. 105°–106°.

2.3 g of 1A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give 1B as a pale yellow solid, m.p. 76°–78°.

A solution of 13.7 g of ethyl chlorothiolformate in 50 ml of dry tetrahydrofuran was added to 9.0 g of 1-methylimidazole in 200 ml of dry tetrahydrofuran at 5°, over a 20-minute period. The mixture was stirred at 5° for 30 minutes, then 16.0 g of 1B was added all at once, and the stirred mixture was allowed to slowly warm to room temperature and stirred overnight. The solvent was stripped, and the residue was dissolved in a mixture of water and methylene chloride. The two phases were separated, the water phase was extracted with methylene chloride, the methylene chloride solutions were combined, dried ($MgSO_4$), filtered and the solvent was evaporated under reduced pressure, to leave an oil. The oil was stirred with a mixture of water and ether; solid material was filtered off and recrystallized from ethyl alcohol to give 1, as a pale yellow solid, m.p.: 124°–124.5°.

EXAMPLE 2

The corresponding methyl ester (2) was prepared in a similar manner, except that it was necessary to reflux the reaction mixture for 6 hours to effect the reaction. 2 was obtained as a tan solid, m.p.: 157°–158°.

EXAMPLE 3

The corresponding 2-(methylthio)ethyl ester (3), was prepared, as a yellow solid, m.p.: 119°–119.5°, from 1B and 2-(methylthio)ethyl chlorothiolformate, in a similar manner.

EXAMPLE 4 dimethyl
(2-(nitro(tetrahydro-2H-1,3-thiazin-2-ylidene)acetylthio)ethyl sulfonium iodide (4)

4, the sulfonium salt of 3, was prepared, as a yellow solid, m.p.: 144.5°–145° (with decomposition), by treating 3 with methyl iodide in acetone, the mixture being allowed to stand for 20 hours at room temperature, then 4 being separated by filtration.

Compounds of this invention exhibit useful insecticidal activity, being of particular interest for control of the larvae "caterpillar" or "worm" forms of insects of the genus Heliothis, such as H. Zea (corn earworm, cotton bollworm, tomato fruitworm), H. virescens (tobacco budworm); the genus Agrotis, such as A. ipsilon (black cutworm); the genus Trichoplusia, such as T. ni (cabbage looper), and the genus Spodoptera, such as S. littoralis (Egyptian cotton leafworm). Some are also of interest for controlling houseflies. In tests that have been conducted they have exhibited low, or no, toxicity to other insects such as the 2-spotted spider mite and mosquito larvae.

Activity of compounds of this invention with respect to insects was determined by using standardized tests to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted spider mite. Activity with respect to mosquito larvae was determined by placing the larvae in water containing the test compound.

All of compounds 1 through 4 were found to be inactive or but slightly active with respect to the mites, aphids and mosquito larvae. With respect to the corn earworm, all of the compounds were found to be active. With respect to the housefly, compounds 1 and 3 were found to be somewhat active.

The invention includes within its scope insecticidal compositions comprising an adjuvant — that is, a carrier optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers; solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of toxicant. Granules may be manufactured by agglomeration or impregnation techniques. Generally, granules will contain ½-25%w toxicant and 0-10%w of additives such as stabilizers, slow release modifiers and binding agents. Emulsifiable concentrates usually contain, in addition to the solvent, and when necessary, co-solvent, 10-50%w/v toxicant, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w toxicant, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A resonance hybrid in which the significant forms are represented by the formulae

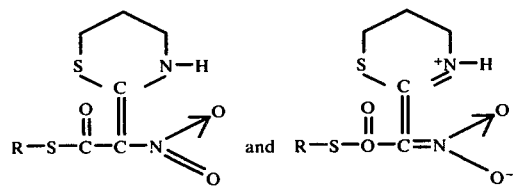

and the enol forms represented by the formula

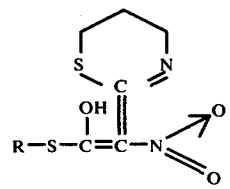

wherein R contains up to thirty carbon atoms and is alkyl, alkenyl, alkynyl, cycloalkyl, cycloalkylalkyl, alkadienyl, haloalkyl, haloalkenyl, mono- and poly-(alkoxy)alkyl, alkylthioalkyl, phenylthioalkyl, benzylthioalkyl, cyanoalkyl, hydroxyalkyl, alkylsulfinylalkyl, alkylsulfonylalkyl, phenyl, phenalkyl, phenylalkenyl or any of these substituted on the ring by one or two of one or more of halogen, nitro, cyano, alkyl, phenyl, alkoxy, methylenedioxy or phenoxy; is aminoalkyl, $(CH_2)_mNR^3R^4$, wherein $m$ is one or two, $R^3$ is alkyl, cycloalkyl, alkenyl, phenyl or phenalkyl, and $R^4$ is hydrogen or one of the moieties represented by $R^3$; or is $(CH_2)_nR^5$, wherein $n$ is zero, one or two, and $R^5$ is a heterocyclic moiety selected from furanyl, tetrahydrofuranyl, dioxolanyl, thienyl, thiopyranyl, pyridinyl, pyrrolidinyl, morpholinyl, and their $R^5$-methyl- counterparts.

2. A method for controlling insects which comprises subjecting them to the action of a resonance hybrid defined in claim 1.

3. An insecticidal composition comprising a resonance hybrid defined in claim 1 together with an insecticidal adjuvant therefor.

* * * * *

UNITED STATES PATENT AND TRADEMARK OFFICE
CERTIFICATE OF CORRECTION

PATENT NO. : 4,024,254
DATED : May 17, 1977
INVENTOR(S) : STEVEN A. ROMAN

It is certified that error appears in the above-identified patent and that said Letters Patent are hereby corrected as shown below:

Column 2, line 3, change the comma after "morpholinyl" to a period and cancel "and their $R^5$-methyl- counter".

Column 2, line 4, cancel all of the line.

Claim 1, right-hand top formula, and bottom formula, in each, change the double bond between the ring-carbon atom and th non-ring carbon atom to a single bond.

Claim 1, line 26, change "forms" to -- form --.

Claim 1, penultimate line, change the comma after "morpholinyl" to a period, and cancel "and their $R^5$-methyl- counter-".

Claim 1, last line, cancel all of the line.

Signed and Sealed this

Twenty-fifth Day of October 1977

[SEAL]

Attest:

RUTH C. MASON
Attesting Officer

LUTRELLE F. PARKER
Acting Commissioner of Patents and Trademar